United States Patent
Horn

(10) Patent No.: US 6,776,161 B2
(45) Date of Patent: Aug. 17, 2004

(54) HEAD HARNESS FOR A RESPIRATOR

(75) Inventor: Michael Horn, Berlin (DE)

(73) Assignee: MSA Auer GmbH, Berlin (DE)

( * ) Notice: Subject to any disclaimer, the term of this patent is extended or adjusted under 35 U.S.C. 154(b) by 0 days.

(21) Appl. No.: 10/469,301

(22) PCT Filed: Jul. 29, 2002

(86) PCT No.: PCT/DE02/02862

§ 371 (c)(1),
(2), (4) Date: Dec. 19, 2003

(87) PCT Pub. No.: WO03/018136

PCT Pub. Date: Mar. 6, 2003

(65) Prior Publication Data

US 2004/0073989 A1 Apr. 22, 2004

(30) Foreign Application Priority Data

Aug. 17, 2001 (DE) .......................................... 101 40 575

(51) Int. Cl.⁷ ............................................. A62B 18/08
(52) U.S. Cl. ........................................ 128/207.11; 2/9
(58) Field of Search ............................... 2/9, 173, 452; 128/207.11, 201.23, 206.12, 206.24, 206.27, 206.23

(56) References Cited

U.S. PATENT DOCUMENTS

| 1,395,761 A | * | 11/1921 | Monroe et al. ........ 128/207.11 |
| 5,038,776 A | * | 8/1991 | Harrison et al. ....... 128/207.11 |
| 5,069,205 A | * | 12/1991 | Urso ...................... 128/201.24 |
| 5,481,763 A | | 1/1996 | Brostrom et al. .............. 2/452 |
| 5,662,101 A | * | 9/1997 | Ogden et al. .......... 128/205.25 |
| 5,669,375 A | * | 9/1997 | Dahrendorf et al. ... 128/206.17 |
| 5,895,537 A | | 4/1999 | Campbell ................... 156/73.1 |
| 6,062,222 A | * | 5/2000 | Lewis et al. ........... 128/207.11 |
| 6,691,314 B1 | * | 2/2004 | Grilliot et al. ..................... 2/5 |

FOREIGN PATENT DOCUMENTS

| DE | 31 22 034 | 12/1982 |
| DE | 297 19 440 | 3/1998 |
| EP | 046 43 42 | 1/1992 |

* cited by examiner

Primary Examiner—Rodney M. Lindsey
(74) Attorney, Agent, or Firm—Miles & Stockbridge P.C.

(57) ABSTRACT

The invention relates to a head harness for a respirator which comprises a head plate (1) that is elastic in the X direction and that is substantially nonelastic in the Y direction. Front straps (2), temple straps (3) and neck straps (4) are fastened to the head plate, only the temple and the neck straps being extensible. The strap buckles (5) provided for fastening the front and temple straps to the mask base are rigidly adjusted according to the head size so that the mask is already correctly positioned and preliminarily fixed when put on and only the neck strap has to be readjusted. The head harness can be adapted to different head shapes and sizes and allows for a high wearing comfort. The respirator can be quickly and easily put on.

6 Claims, 1 Drawing Sheet

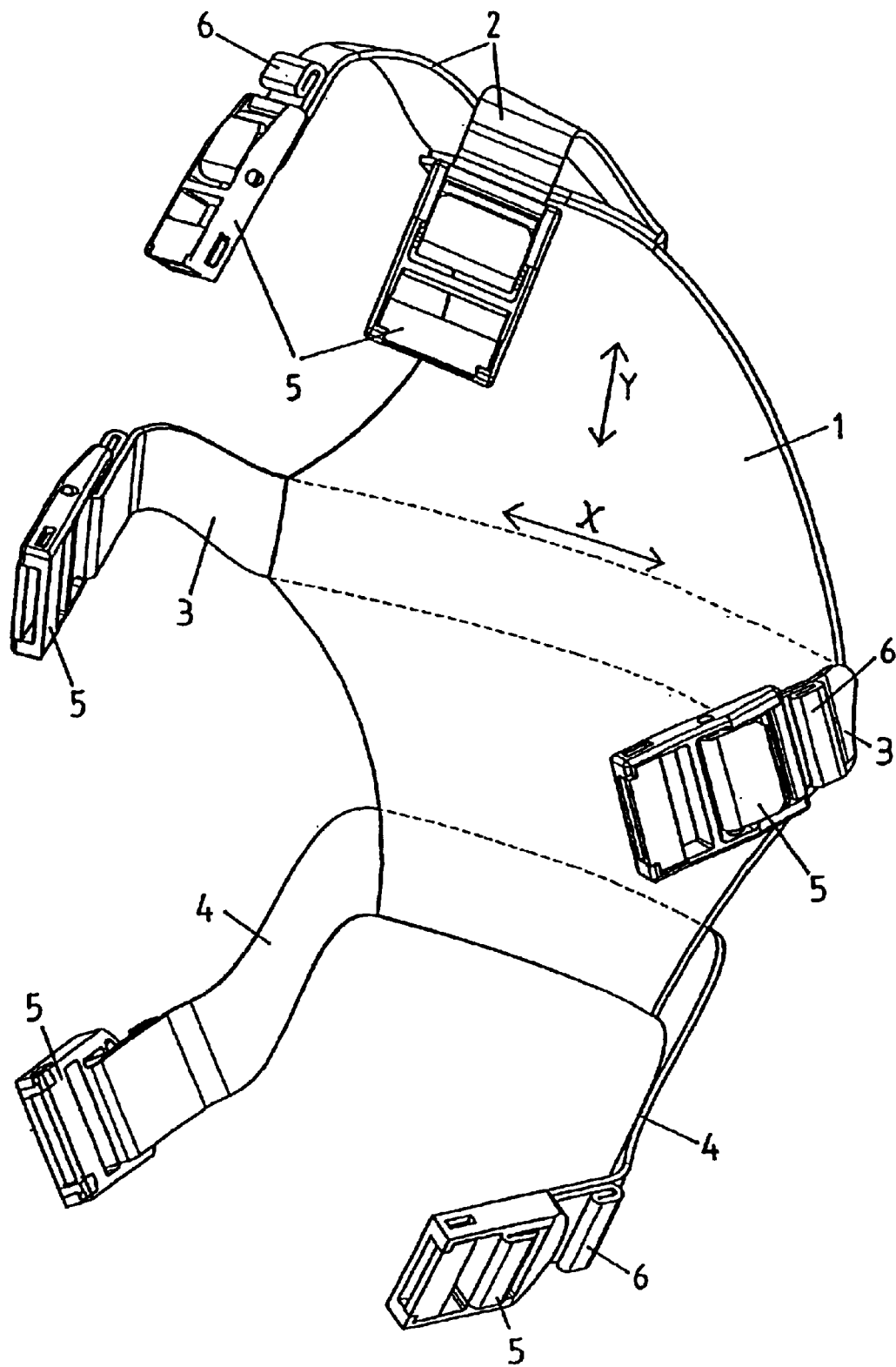

HEAD HARNESS FOR A RESPIRATOR

The invention relates to a head harness for a respiratory mask that consists of a head plate and front, temple, and neck straps emerging from it that can be fastened to the respiratory mask with strap buckles in a six-point strap arrangement.

A similar head harness with a five-point strap arrangement in which one elastic strap in the forehead area, two elastic temple straps and two fixed straps across the neck emerge from a firm, inflexible head plate has been disclosed in EP 046 43 42, for example. The fixed neck straps are connected to the mask body by adjustable screws. Wearing a mask of this type is not sufficiently comfortable as the head harness of the respiratory mask may loosen and continuously needs readjustment to achieve safe fastening of the mask. This means that a firm fit of the mask is not guaranteed, especially under strain, as the mask easily slips under strain due to the elastic front strap. But if the straps are pulled too tight, they limit the head's freedom of motion. The non-elastic head plate won't slip when the mask is put on.

To hold the respiratory mask known from EP 0350 322 on the wearer's head, it features a biaxially stretchable cap composed of multiple parts and domed to fit the shape of the head, while the head harness is mostly directly connected to the mask body. This head harness that encloses the head like a cap is sufficiently elastic to adapt to the shape of the head, however it does not ensure a firm fit when a respiratory filter is attached so that the mask can slip when in use, which reduces wearing comfort.

It is the problem of this invention to provide a head harness of the type mentioned at the outset for a respiratory mask that ensures a good fit of the straps for various head sizes while allowing free movement of the head and a firm fit as well as convenient and fast donning of the mask.

This problem is solved according to the invention by the head harness comprising the characteristics described in claim 1.

The subordinate claims disclose further characteristics and advantageous improvements of the invention.

Starting from the known head harness with a six-point strap fastening arrangement to the mask body wherein front, temple, and neck straps emerge from a head plate and connect to the mask, the general inventive idea here is that the head plate consists of a knitted fabric that is elastic in crosswise direction (X direction) only while it cannot be stretched in longitudinal direction (Y direction). The temple and neck straps that run in crosswise direction can also be stretched in this direction. The front strap that runs in longitudinal direction, however, is not elastic.

A head harness of this design is capable of compensating for differing head sizes, adjusting to different head shapes, and ensuring a firm fit and high wearing comfort. The forces that act in crosswise direction are evenly distributed across the elastic head plate while the longitudinal forces that act on the mask body are transmitted via the rigid front straps and absorbed by the head plate. As the forces are distributed elastically across the head plate, the mask fits firmly to its wearer's face, and any longitudinal forces that occur are absorbed. Freedom of movement of the head is not reduced despite the tight-fitting respiratory mask.

In another aspect of the invention, the head and temple straps that emerge from the head plate can be fixedly preset to the respective head size and shape while only the neck straps are tightened after the wearer has put the mask on. In this way, the respiratory mask is correctly positioned and preset automatically after being put on. The neck straps are then tightened to the point at which the respiratory mask and head harness have a firm and comfortable fit on the head.

Another important characteristic of the invention is that each of the front, temple, and neck straps is a single, continuous strap. This distributes the forces in crosswise direction and the transmission of forces in longitudinal direction more evenly and increases the service life of the straps.

In an embodiment of the invention, the head plate is made of a heat and chemical-resistant knitted fabric known by the trade name NOMEX® that has the expansion characteristics described above and the shape of a double trapezoid along the upper rim of which the front strap runs, along the lower rim of which the neck strap runs, and along the joint elongated base line of the two trapezoids, i.e., along its widest section, the temple strap runs.

An embodiment of the invention is explained in greater detail below with reference to the FIGURE. The only FIGURE shows a perspective view of a head harness with a six-point fastening arrangement to the mask body.

The head harness consists of a head plate 1 as well as a front strap 2, a temple strap 3, and a neck strap 4. The head plate 1 has the shape of a double trapezoid, i.e. of two trapezoids that abut at their long base edges. It consists of a non-combustible, chemically and temperature stable knitted fabric that is known by the trade name NOMEX®. An important characteristic of the head plate 1 or the knitted fabric used for making it, respectively, is that it is highly elastic in crosswise direction but substantially not expandable in longitudinal direction. Each of the front strap 2, the temple strap 3, and the neck strap 4 is a single continuous strap with NOMEX knitted fabric woven around it that is attached to the side of the head plate that faces away from the wearer's head. The front strap 2 that is connected to the mask body (not shown) at two points consists of a non-stretchable base material. Its entire surface that runs across the head plate 1 is sewed in crosswise direction to the upper rim of the head plate 1 while its free ends run in longitudinal direction of the head plate 1. This creates a stable joint of the head plate 1 and the mask body (not shown). This means that the respiratory mask cannot slip downwards under the typical strains when used even with the added weight of a filter attached to the mask body because there is no longitudinal expansion and the head plate 1 is fixed and elastically prestressed in crosswise direction. Not only the head plate 1 but also the temple strap 3 and the neck strap 4 can be stretched to ensure the elastic effect in crosswise direction on the mask body (not shown). Strap buckles that connect to the mask body are provided on the two free ends of each strap (front strap 2, temple strap 3, and neck strap 4), and the strap buckles are used to fixedly preset the length of the front strap 2 and the temple strap 3 to fit the size and shape of the wearer's head. Thus a user-specific exact fit is preset in the upper section of the head harness, i.e. using the upper four attachment points. The strap buckles on the neck strap 4 are not fixedly preset but are positioned to produce a long neck strap length so that the mask can be donned fast and comfortably. The respiratory mask is fixed horizontally and in longitudinal direction to the user's head after tightening the two neck strap parts. However, the elasticity of the neck strap 4 lets the user move his or her head without any obstruction. After sliding on the strap buckles, the two ends of the front strap 2, the temple strap 3, and the neck strap 4 are hemmed to form a bulge 6 so that the strap ends cannot slide out of the respective strap buckle. As the straps are made in one piece and provided with a bulge 6 on their free ends, no open strap ends are left where the rubber threads in the elastic temple and neck straps 3, 4 could be pulled out.

| List of reference symbols | |
|---|---|
| 1 | head plate |
| 2 | front strap |
| 3 | temple strap |
| 4 | neck strap |
| 5 | strap buckle |
| 6 | bulge |

What is claimed is:

1. A head harness for a respiratory mask consisting of a head plate and front, temple, and neck straps emerging from it that can be fastened with strap buckles to the mask body in a six-point arrangement, characterized in that the head plate (1) is made of a material than can be elastically expanded in crosswise direction (x) but is substantially non-expandable in longitudinal direction (y) and in that the temple and neck straps (3, 4) that extend crosswise (x) from the head plate (1) can also be stretched in this direction while the front straps (2) that emerge from the upper rim of the head plate (1) consist of a rigid, non-expandable material.

2. The head harness according to claim 1, characterized in that the length of the front straps (2) and the temple straps (3) can be preset to the user's head size for correct positioning and preadjustment of the respiratory mask and harness using the strap buckles while the strap buckles of the neck straps (4) are used for tightening the neck straps (4) and for final mask fastening.

3. The head harness according to claim 1, characterized in that the front strap (2), the temple strap (3), and the neck strap (4) each consist of a single continuous strap that runs in crosswise direction (x) and is attached to the side of the head plate (1) that faces away from the wearer's head.

4. The head harness according to claim 1, characterized in that the ends of the front, temple, and neck straps (4) are flipped over to form a bulge (6) and closed at the front.

5. The head harness according to any claim 1, characterized in that the head plate (1) that can be stretched crosswise consists of a knitted fabric.

6. The head harness according to claim 1, characterized in that the head plate (1) has the shape of two trapezoids abutting along their base lines while the front strap (2) runs at its upper rim, the neck strap (4) on its lower rim, and the temple strap (3) runs along the abutting base lines of the double trapezoid.

* * * * *